United States Patent
Govari et al.

(10) Patent No.: US 8,374,819 B2
(45) Date of Patent: Feb. 12, 2013

(54) ACTUATOR-BASED CALIBRATION SYSTEM FOR A PRESSURE-SENSITIVE CATHETER

(75) Inventors: Assaf Govari, Haifa (IL); Yaron Ephrath, Karkur (IL); Andres Claudio Altmann, Haifa (IL)

(73) Assignee: Biosense Webster (Israel), Ltd., Yokneam (IL)

( * ) Notice: Subject to any disclaimer, the term of this patent is extended or adjusted under 35 U.S.C. 154(b) by 432 days.

(21) Appl. No.: 12/646,050

(22) Filed: Dec. 23, 2009

(65) Prior Publication Data

US 2011/0153252 A1    Jun. 23, 2011

(51) Int. Cl.
 *G01L 1/04* (2006.01)
(52) U.S. Cl. ......... 702/104; 702/41; 702/150; 600/424
(58) Field of Classification Search .......... 702/85, 702/98, 104, 41–44, 150, 152, 153; 600/463, 600/407, 424
See application file for complete search history.

(56) References Cited

U.S. PATENT DOCUMENTS

| | | | |
|---|---|---|---|
| 5,391,199 A | 2/1995 | Ben-Haim | |
| 6,239,724 B1 | 5/2001 | Doron et al. | |
| 6,332,089 B1 | 12/2001 | Acker et al. | |
| 6,335,617 B1 | 1/2002 | Osadchy et al. | |
| 6,484,118 B1 | 11/2002 | Govari | |
| 6,618,612 B1 | 9/2003 | Acker et al. | |
| 6,690,963 B2 | 2/2004 | Ben-Haim et al. | |
| 6,695,808 B2 | 2/2004 | Tom | |
| 6,915,149 B2 | 7/2005 | Ben-Haim | |
| 7,397,364 B2 * | 7/2008 | Govari | 340/539.12 |
| 8,083,691 B2 * | 12/2011 | Goldenberg et al. | 600/587 |
| 2002/0065455 A1 | 5/2002 | Ben-Haim et al. | |
| 2003/0120150 A1 | 6/2003 | Govari | |
| 2004/0068178 A1 | 4/2004 | Govari | |
| 2004/0254458 A1 | 12/2004 | Govari | |
| 2007/0021742 A1 | 1/2007 | Viswanathan | |
| 2007/0100332 A1 | 5/2007 | Paul et al. | |
| 2008/0183075 A1 | 7/2008 | Govari et al. | |
| 2009/0093806 A1 | 4/2009 | Govari et al. | |
| 2009/0138007 A1 | 5/2009 | Govari et al. | |

FOREIGN PATENT DOCUMENTS

WO    WO 96/05768    2/1996
WO    97/29678 A2    8/1997

OTHER PUBLICATIONS

EP Search Report No. EP 10 25 2189 Dated Mar. 15, 2011.

* cited by examiner

*Primary Examiner* — Manuel L Barbee
(74) *Attorney, Agent, or Firm* — William A. Schoneman

(57) ABSTRACT

A calibration apparatus includes a fixture coupled to hold a distal end of a medical probe. An actuator is configured to press against the distal tip of the probe and apply to the distal tip multiple force vectors having respective magnitudes and angles with respect to the distal end, so as to cause a deformation of the distal tip relative to the distal end. A sensing device is configured to measure the magnitudes of the force vectors applied by the actuator. A calibration processor is configured to receive from the probe first measurements indicative of the deformation of the distal tip in response to the force vectors, to receive from the sensing device second measurements indicative of the magnitudes of the force vectors, and to compute, based on the angles and the first and second measurements, calibration coefficients for assessing the force vectors as a function of the first measurements.

16 Claims, 4 Drawing Sheets

ACTUATOR-BASED CALIBRATION SYSTEM FOR A PRESSURE-SENSITIVE CATHETER

FIELD OF THE INVENTION

The present invention relates generally to invasive probes, and specifically to calibrating pressure sensors in invasive probes.

BACKGROUND

A wide range of medical procedures involve placing objects, such as sensors, tubes, catheters, dispensing devices and implants, within the body. Position sensing systems have been developed for tracking such objects. Magnetic position sensing is one of the methods known in the art. In magnetic position sensing, magnetic field generators are typically placed at known positions external to the patient. A magnetic field sensor within the distal end of a probe generates electrical signals in response to these magnetic fields, which are processed in order to determine the position coordinates of the distal end of the probe. These methods and systems are described in U.S. Pat. Nos. 5,391,199, 6,690,963, 6,484,118, 6,239,724, 6,618,612 and 6,332,089, in PCT International Publication WO 1996/005768, and in U.S. Patent Application Publications 2002/0065455 A1, 2003/0120150 A1 and 2004/0068178 A1, whose disclosures are all incorporated herein by reference.

When placing a probe within the body, it may be desirable to have the distal tip of the probe in direct contact with body tissue. The contact can be verified, for example, by measuring the contact pressure between the distal tip and the body tissue. U.S. Patent Application Publications 2007/0100332, 2009/0093806 and 2009/0138007, whose disclosures are incorporated herein by reference, describe methods of sensing contact pressure between the distal tip of a catheter and tissue in a body cavity using a force sensor embedded in the catheter. The distal tip of the catheter is coupled to the distal end of the catheter insertion tube by a resilient member, such as a spring, which deforms in response to force exerted on the distal tip when it presses against endocardial tissue. A magnetic position sensor within the catheter senses the deflection (location and orientation) of the distal tip relative to the distal end of the insertion tube. Movement of the distal tip relative to the insertion tube is indicative of deformation of the resilient member, and thus gives an indication of the pressure.

SUMMARY OF THE INVENTION

An embodiment of the present invention provides a calibration apparatus including a fixture, an actuator, a sensing device and a calibration processor. The fixture is coupled to hold a distal end of a medical probe. The actuator is configured to press against the distal tip of the probe and apply to the distal tip multiple force vectors having respective magnitudes and angles with respect to the distal end of the probe, so as to cause a deformation of the distal tip relative to the distal end. The sensing device is configured to measure the magnitudes of the force vectors applied by the actuator The calibration processor is configured to receive from the probe first measurements indicative of the deformation of the distal tip in response to the force vectors, to receive from the sensing device second measurements indicative of the magnitudes of the force vectors, and to compute, based on the angles and the first and second measurements, calibration coefficients for assessing the force vectors as a function of the first measurements.

In some embodiments, the apparatus includes a planar surface coupled to the actuator and configured to press against the distal tip of the probe. In a disclosed embodiment, the distal end of the probe includes a field generator that generates a magnetic field, and the distal tip includes a field sensor that senses the magnetic field and produces the first measurements in response to the sensed magnetic field. In another embodiment, the apparatus includes multiple field generators, which are external to the probe and are operative to generate respective magnetic fields, and the distal end and the distal tip of the probe include respective first and second field sensors that sense the magnetic fields so as to produce the first measurements.

In yet another embodiment, the apparatus includes a jig, which holds the actuator and is controlled by the calibration processor so as to apply the force vectors at the respective magnitudes and angles. In still another embodiment, the fixture is configured to allow the probe to be rotated with respect to a longitudinal axis of the probe, and the calibration processor is configured to detect an axial asymmetry in the deformation of the distal tip by processing the first measurements received from the rotated probe. In an embodiment, the calibration processor is configured to store the calibration coefficients in a memory that is coupled to the probe. The memory may include an Electronically Erasable Programmable Read Only Memory (E2PROM).

There is also provided, in accordance with an embodiment of the present invention, a method of calibrating, including holding a distal end of a medical probe having a distal tip in a fixture, pressing an actuator against the distal tip so as to apply to the distal tip multiple force vectors having respective magnitudes and angles with respect to the distal end of the probe and cause a deformation of the distal tip relative to the distal end, receiving from the probe first measurements indicative of the deformation of the distal tip in response to the force vectors, receiving from a sensing device coupled to the actuator second measurements indicative of magnitudes of the force vectors, and computing, based on angles and the first and second measurements, calibration coefficients for assessing the force vectors as a function of the first measurements.

BRIEF DESCRIPTION OF THE DRAWINGS

The disclosure is herein described, by way of example only, with reference to the accompanying drawings, wherein.

DETAILED DESCRIPTION OF EMBODIMENTS

Figure 1:
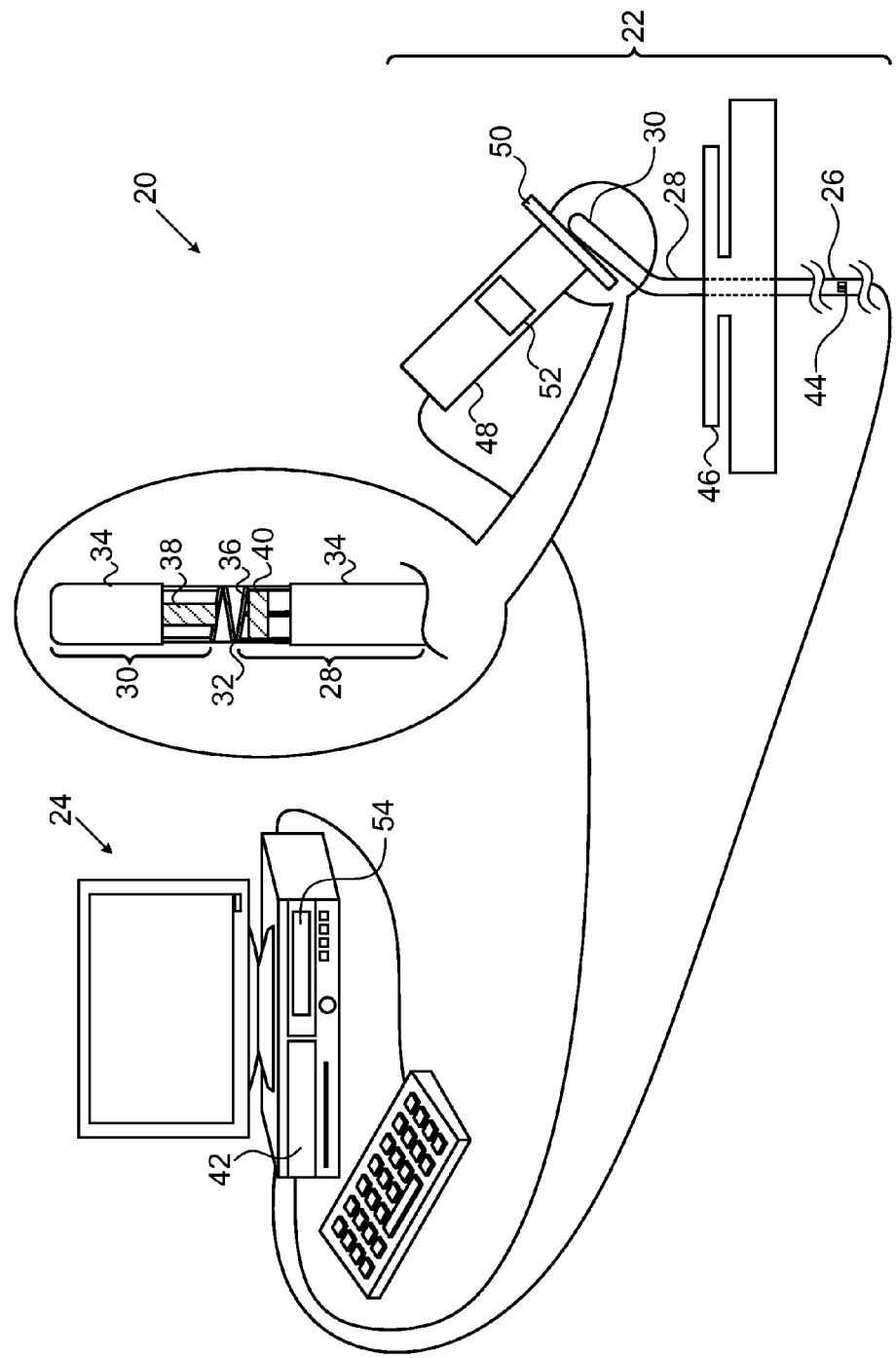
FIG. 1 is a schematic pictorial illustration of a calibration system for a pressure-sensitive catheter, in accordance with an embodiment of the present invention.

Some invasive probes comprise pressure sensors for measuring the contact pressure between the probe and intra-body tissue. For example, the distal tip of a cardiac catheter may comprise a pressure sensor, which deforms in response to the pressure exerted by the distal tip on the endocardial tissue. A position sensor in the catheter measures the deflection of the distal tip, and thus provides an indication of the contact pressure. In many practical cases, however, the relationship between the actual contact pressure and the reading of the position sensor varies from one catheter to another.

In order to ensure accurate pressure measurements, embodiments of the present invention provide methods and systems for calibrating probes (e.g., catheters) fitted with pressure sensors. In some embodiments, a calibration apparatus comprises a fixture for mounting a catheter, an actuator with a planar surface for pressing against the distal tip of the catheter, and a pressure gauge coupled to the actuator for measuring the force exerted by the actuator on the distal tip. The actuator can be positioned and oriented automatically to contact the catheter tip from a variety of angles, and thus may apply mechanical force on the distal tip both longitudinally and obliquely (in order to model both head-on and oblique contact between the catheter and the body tissue). In some embodiments, the catheter may be rotated in the fixture in order to detect axial asymmetry in the pressure response of the catheter.

The calibration apparatus may be configured, as part of the calibration procedure, to apply a desired range of forces to the distal tip of the catheter from a variety of angles. As the actuator applies known forces to the distal tip, the calibration apparatus records signals from the position sensor in the catheter in order to determine the calibration parameters.

When the actuator applies multiple force vectors having respective angles and magnitudes to the catheter, the distal tip deforms in response to these force vectors, and the pressure sensor in the catheter produces deformation (i.e., deflection) measurements of its distal tip. A calibration processor accepts the deformation measurements from the catheter and the pressure measurements from the actuator's pressure gauge. Based on the deformation measurements and the known force vectors, the calibration processor computes calibration coefficients for assessing the force vector as a function of the tip deformation. Thus, pressure-sensing catheters may be calibrated over the entire expected range of conditions of tissue contact. Additionally, the calibration processor may detect and compensate for variations of pressure response by different catheters during the calibration procedure.

In some embodiments, the actuator is controlled by the calibration processor. To calibrate a given catheter, the calibration processor may direct the actuator to apply a desired set of force vectors (i.e., a variety of forces at multiple angles) to the catheter tip. Additionally or alternatively, an operator may position the actuator manually against the catheter tip to cause the deformation.

In some embodiments, the calibration coefficients are stored as a calibration matrix in a non-volatile memory that is coupled to the catheter. When the catheter is later used in a medical system, the actual pressure exerted by the catheter's distal tip on the body tissue can be derived with high accuracy from the deflection measurements, using the calibration coefficients stored in the matrix.

FIG. 1 is an illustration of a calibration system 20 for a pressure-sensitive catheter, in accordance with an embodiment of the present invention. System 20 comprises a calibration apparatus 22 coupled to a calibration unit 24. In the embodiment described hereinbelow, system 20 is used for calibrating a probe, in the present example a catheter 26 for therapeutic and/or diagnostic purposes in a heart or in other body organs.

Catheter 26 comprises a distal end 28, with a distal tip 30 connected to the distal end via a joint 32. Applying sufficient pressure to distal tip 30 (or conversely, if the distal tip applies sufficient pressure against a surface, such as body tissue), catheter 26 will bend at joint 32, thereby deflecting distal tip 30 relative to distal end 28.

Distal end 28 and distal tip 30 of the catheter are both covered by a flexible, insulating material 34. The area of joint 32 is covered, as well, by a flexible, insulating material, which may be the same as material 34 or may be specially adapted to permit unimpeded bending and compression of the joint, (This material is cut away in FIG. 1 in order to expose the internal structure of the catheter.) Distal tip 30 is typically relatively rigid, by comparison with distal end 28.

Distal tip 30 is connected to distal end 28 by a resilient member 36. In FIG. 1, the resilient member has the form of a coil spring, but other types of resilient components may alternatively be used for this purpose. Resilient member 36 permits a limited range of relative movement between tip 30 and distal end 28 in response to forces exerted on the distal tip.

Distal tip 30 contains a magnetic position sensor 38. Sensor 38 may comprise one or more miniature coils, and typically comprises multiple coils oriented along different axes. Distal end 28 comprises a miniature internal magnetic field generator 40 near resilient member 36. Typically, field generator 40 comprises a coil, which is driven by a current conveyed through the catheter from calibration unit 24.

Alternatively, position sensor 38 may comprise either another type of magnetic sensor, an electrode which serves as a position transducer, or position transducers of other types, such as impedance-based or ultrasonic position sensors. Although FIG. 1 shows a probe with a single position sensor, additional embodiments of the present invention described infra may utilize probes with more than one position sensor.

The magnetic field created by field generator 40 causes the coils in sensor 38 to generate electrical signals at the drive frequency of the field generator. The amplitudes of these signals will vary depending upon the location and orientation of distal tip 30 relative to distal end 28. A calibration processor in calibration unit 24 processes these signals in order to determine the axial displacement and the magnitude of the angular deflection of distal tip 30 relative to distal end 28. (Because of the axial symmetry of the field generated by a coil, only the magnitude of the deflection can be detected using a single coil in field generator 40, and not the direction of the deflection. Optionally, field generator 40 may comprise two or more coils, in which case the direction of deflection may be determined, as well). The magnitudes of the displacement and deflection may be combined by vector addition to give a total magnitude of the movement of distal tip 30 relative to distal end 28.

The relative movement of distal tip 30 relative to distal end 28 gives a measure of the deformation of resilient member 36. Thus, the combination of field generator 40 with sensor 38 serves as a pressure sensing system. By virtue of the combined sensing of displacement and deflection, this pressure sensing system reads the pressure correctly regardless of whether the pressure is exerted on distal tip 30 head-on or at an angle. Further details of this sort of probe and position sensor are described in U.S. Patent Application Publications 2007/0100332, 2009/0093806 and 2009/0138007, cited above.

In some embodiments, catheter 26 also comprises a non-volatile memory 44, such as electronically erasable programmable read only memory ($E^2PROM$), which stores calibration coefficients computed during calibration. As discussed supra, when the catheter is later used in a medical system, the actual pressure exerted by the catheter's distal tip on body tissue can be derived with high accuracy from deflection measurements, using the calibration coefficients stored in memory 44.

Calibration apparatus 22 comprises a fixture 46 configured to hold the distal end of catheter 26, an actuator 48 with a planar surface 50, and a sensing device 52 such as a pressure gauge coupled to the actuator. As discussed supra, catheter 26 may be rotated in fixture 46 in order to detect axial asymmetry in the pressure response of the catheter. In some embodiments, calibration unit 24 may control the rotation of catheter 26 in fixture 46. Alternatively, an operator (not shown) may manually rotate the catheter in the fixture.

For a given position of actuator 48, the actuator presses planar surface 50 against distal tip 30, thereby applying a given force on the distal tip from a given angle. Pressure gauge 52 measures the magnitude of the force exerted by actuator on distal tip 30. Calibration unit 24 meanwhile receives signals from position sensor 38, which are indicative of the deflection of the distal tip. Calibration processor 42 in the calibration unit calculates calibration coefficients that map the measured tip deflection to the known force vector applied by the actuator.

Actuator 48 and probe 26 are connected to calibration unit via suitable interfaces (e.g., cables and connectors). Calibration unit 24 comprises calibration processor 42, and a memory 54. Processor 42 typically comprises a general-purpose computer, with suitable front end and interface circuits for receiving signals from position sensor 38 and pressure gauge 50, as well as for controlling the force vectors applied by actuator 48. Processor 42 may be programmed in software to carry out the functions that are described herein. The software may be downloaded to processor 42 in electronic form, over a network, for example, or it may be provided on tangible media, such as optical, magnetic or electronic memory media. Alternatively, some or all of the functions of processor 42 may be carried out by dedicated or programmable digital hardware components.

In some embodiments, actuator 48 is mounted in a robotic jig (not shown in the figure), which positions the actuator at a desired position and angle with respect to the distal end of catheter 26. The robotic jig may comprise any suitable mechanical and electrical components, such as electrical motors, for positioning and orienting actuator 48. Typically, the robotic jig is controlled by calibration processor 42, so as to cause the actuator to apply the desired force vectors to the catheter tip.

Figure 2:
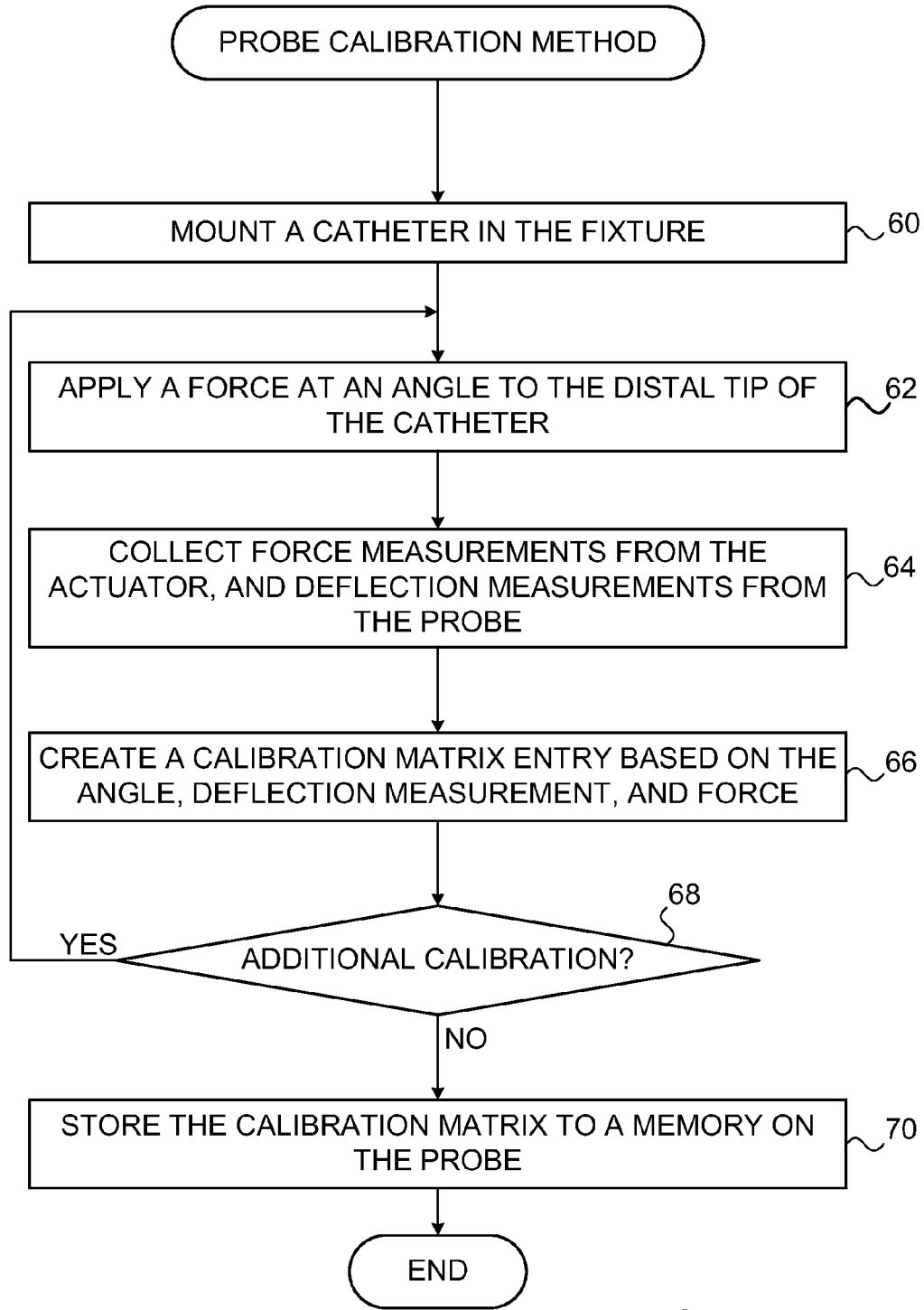
FIG. 2 is a flow diagram that schematically illustrates a method of calibrating a pressure-sensitive catheter, in accordance with an embodiment of the present invention.

FIG. 2 is a flow diagram that schematically illustrates a method of calibrating a pressure-sensitive catheter, in accordance with an embodiment of the present invention. To calibrate catheter 26, the operator mounts the catheter in fixture 44 (step 60). Actuator 48 presses planar surface 50 against distal tip 30 at an angle (step 62). Pressing planar surface 50 against distal tip 30 causes catheter 26 to bend at joint 32, thereby deflecting the distal tip. Position sensor 38 at distal tip 30 outputs a signal indicative of the deflection of the distal tip relative to distal end 28.

Calibration unit 24 accepts the deflection measurements from position sensor 38, and the force measurements from pressure gauge 52 (step 64).

Processor 42 then computes a calibration coefficient for calibrating the deflection measurements of probe 26 based on the force measurement, the engagement angle and the deflection measurement (step 66). By mapping a deflection measurement against a force vector from pressure gauge 52 at a given engagement angle, the calibration coefficient determines the force on distal tip 30 based on the deflection measurement. In other words, a given calibration coefficient translates the deflection measurement of tip 30 into an actual pressure reading, for a given engagement angle.

If more calibration points are desired (step 68), then the method returns to step 62 above, where calibration processor 42 may direct actuator 48 to apply a different force vector against distal tip 30. Employing a variety of force vectors with a range of different magnitudes and directions (i.e., angles) enables system 20 to test a catheter's bend response over a wide range of operating geometries. Returning to step 68, if no more calibration points are required, processor 42 stores a calibration matrix of the calibration coefficients to memory 44 on the probe (step 70), and the method terminates.

Figure 3:
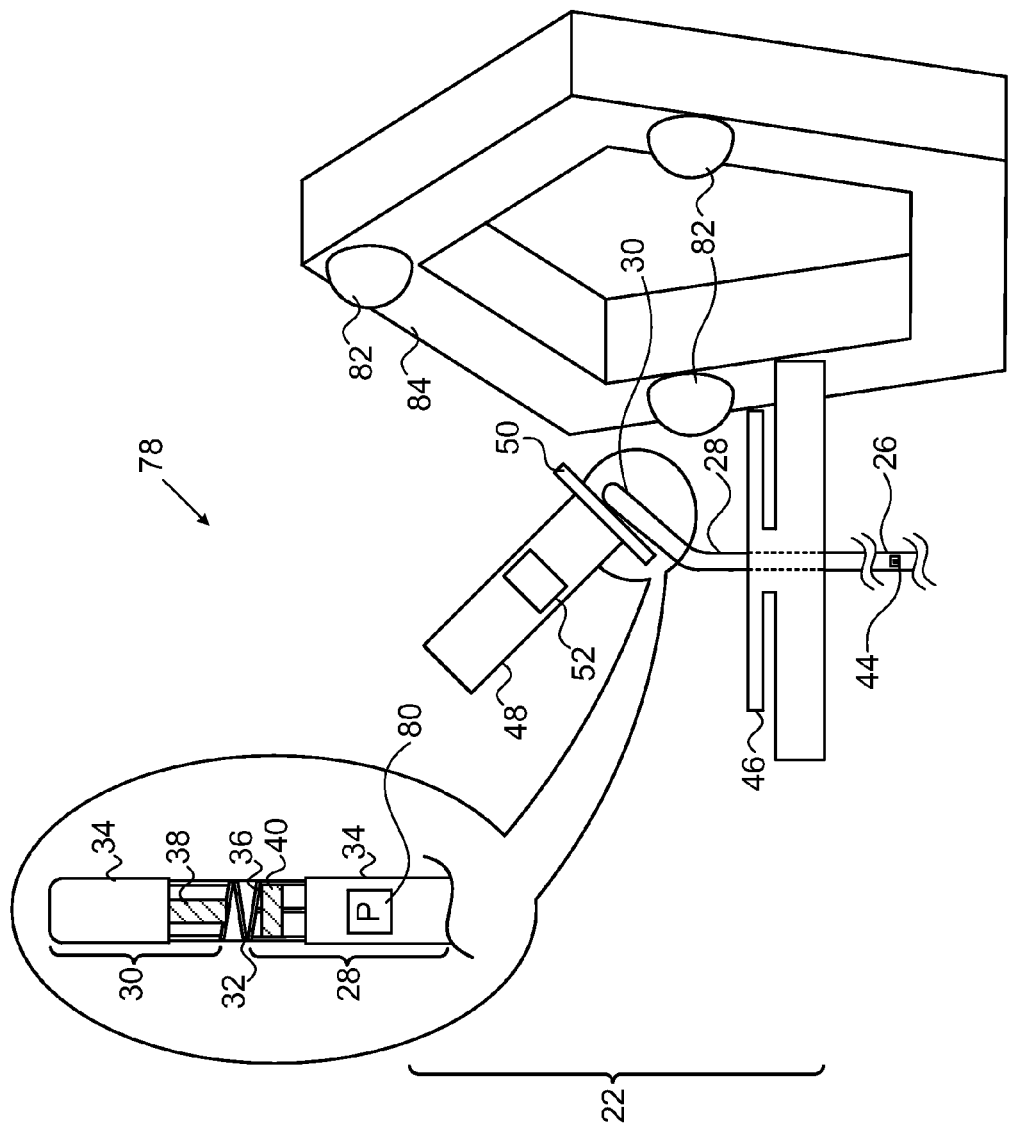
FIG. 3 is a schematic pictorial illustration of a calibration system for a pressure-sensitive catheter, in accordance with an alternative embodiment of the present invention.

FIG. 3 is an illustration of a calibration system 78 for a pressure-sensitive catheter, in accordance with an alternative embodiment of the present invention. In system 78, distal end 28 of catheter 26 comprises a second position sensor 80, for finding the position and orientation coordinates of the distal end. Position sensor 80 is used in conjunction with external magnetic field generators 82, which are typically installed on a mount 84, such as a CARTO™ location pad produced by Biosense Webster Inc. (Diamond Bar, Calif.). The CARTO™ location pad and position sensors 38 and 80 may be used to determine both the position of distal end 28, and the deflection of distal tip 30.

Field generators 82 create magnetic fields that are distinguishable in time and/or frequency from the field generated by field generator 40. For example, the current to field generator 40 may be generated at a selected frequency in the range between about 16 kHz and 25 kHz, while field generators 82 are driven at different frequencies. Additionally or alternatively, the operation of generators 40 and 82 may be time-multiplexed.

A driver circuit (for example, in calibration unit 24) drives field generators 82 (typically comprising coils) to generate magnetic fields. Position sensors 38 and 80 generate electrical signals in response to these magnetic fields. Processor 42 in calibration unit 24 processes the signals received from position sensors 38 and 80, in order to determine the position and orientation coordinates of the two position sensors (and therefore of distal tip 30 and of distal end 28. Further aspects of position tracking using the above-mentioned CARTO™ location pad are described in detail in U.S. Pat. Nos. 5,391,199, 6,690,963, 6,484,118, 6,239,724, 6,618,612 and 6,332,089, in PCT International Publication WO 1996/005768, and in U.S. Patent Application Publications 2002/0065455 A1, 2003/0120150 A1 and 2004/0068178 A1, cited supra.

Returning to step 64 in FIG. 2, in embodiments comprising the CARTO™ location pad (or any other suitable configuration of magnetic field generators), position sensors 38 and 80 output signals indicative of the location of distal tip 30 and distal end 28, respectively. Likewise in step 66, processor 42 may use the signals produced by position sensors 38 and 80 to calculate the deflection of distal tip 30 in relation to distal end 28.

Additionally, processor 42 can compare the outputs of position sensors 38 and 80 in order to detect undesired bending of catheter 26. For example, when force is exerted on distal tip 30 in the longitudinal direction (i.e., along the catheter axis), resilient member 36 may compress, so that the distal tip moves longitudinally closer to distal end 28 but does not bend. If the outputs from position sensors 38 and 80 indicate that distal tip 30 has bent or buckled, processor 42 may identify this behavior as a sign of a fault in the catheter being calibrated or in the calibration procedure. The processor may trigger an alert or otherwise indicate the suspected fault.

Figure 4:
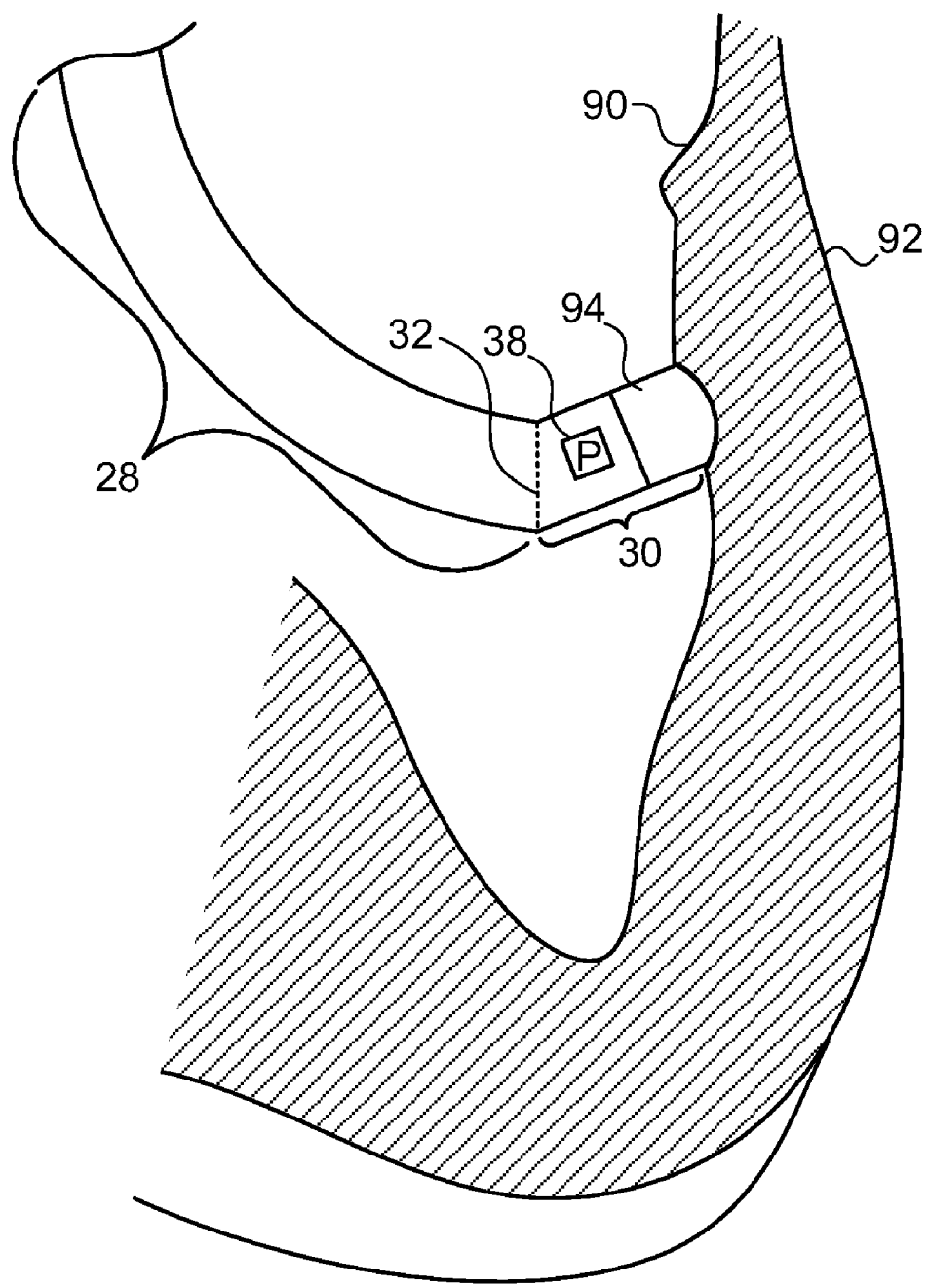
FIG. 4 is a schematic detail view showing the distal tip of a pressure-sensitive catheter in contact with endocardial tissue, in accordance with an embodiment of the present invention.

FIG. 4 is a schematic detail view showing distal tip 30 in contact with an endocardial tissue 90 of a heart 92, in accordance with an embodiment of the present invention. In the present example, tip 30 comprises an electrode 94. In some electrophysiological diagnostic and therapeutic procedures, such as intracardiac electrical mapping, it is important to maintain the proper level of force between electrode 94 and tissue 90. As a medical professional (not shown) presses distal tip 30 against endocardial tissue 90, catheter 26 bends at joint 32. Sufficient force is needed in order to ensure good electrode contact between the distal tip and the tissue. Poor electrical contact can result in inaccurate readings. On the other hand, excessive force can deform the tissue and thus distort the map.

When tip 30 presses against tissue 90, position sensor 38 produces measurements that are indicative of the deflection of tip 30 with respect to distal end 28. The medical imaging system (e.g., mapping system—not shown) translates these measurements into accurate pressure readings using the calibration coefficients (i.e., the calibration matrix) stored in memory 44 of the probe. Thus, calibration of the invasive probe using embodiments of the present invention ensures that the medical professional can accurately control the force exerted by the probe on the tissue.

The corresponding structures, materials, acts, and equivalents of all means or steps plus function elements in the claims below are intended to include any structure, material, or act for performing the function in combination with other claimed elements as specifically claimed. The description of the present disclosure has been presented for purposes of illustration and description, but is not intended to be exhaustive or limiting to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

It is intended that the appended claims cover all such features and advantages of the disclosure that fall within the spirit and scope of the present disclosure. As numerous modifications and changes will readily occur to those skilled in the art, it is intended that the disclosure not be limited to the limited number of embodiments described herein. Accordingly, it will be appreciated that all suitable variations, modifications and equivalents may be resorted to, falling within the spirit and scope of the present disclosure.

What is claimed is:

1. A calibration apparatus, comprising:
   a fixture coupled to hold a distal end of a medical probe;
   an actuator, which is configured to press against the distal tip of the probe and apply to the distal tip multiple force vectors having respective magnitudes and angles with respect to the distal end, so as to cause a deformation of the distal tip relative to the distal end;
   a sensing device, which is configured to measure the magnitudes of the force vectors applied by the actuator; and
   a calibration processor, which is configured to receive from the probe first measurements indicative of the deformation of the distal tip in response to the force vectors, to receive from the sensing device second measurements indicative of the magnitudes of the force vectors, and to compute, based on the angles and the first and second measurements, calibration coefficients for assessing the force vectors as a function of the first measurements.

2. The apparatus according to claim 1, and comprising a planar surface coupled to the actuator and configured to press against the distal tip of the probe.

3. The apparatus according to claim 1, wherein the distal end of the probe includes a field generator that generates a magnetic field, and wherein the distal tip includes a field sensor that senses the magnetic field and produces the first measurements in response to the sensed magnetic field.

4. The apparatus according to claim 1, and comprising multiple field generators, which are external to the probe and are operative to generate respective magnetic fields, and wherein the distal end and the distal tip of the probe include respective first and second field sensors that sense the magnetic fields so as to produce the first measurements.

5. The apparatus according to claim 1, and comprising a jig, which holds the actuator and is controlled by the calibration processor so as to apply the force vectors at the respective magnitudes and angles.

6. The apparatus according to claim 1, wherein the fixture is configured to allow the probe to be rotated with respect to a longitudinal axis of the probe, and wherein the calibration processor is configured to detect an axial asymmetry in the deformation of the distal tip by processing the first measurements received from the rotated probe.

7. The apparatus according to claim 1, wherein the calibration processor is configured to store the calibration coefficients in a memory that is coupled to the probe.

8. The apparatus according to claim 7, wherein the memory comprises an Electronically Erasable Programmable Read Only Memory.

9. A method of calibrating, comprising:
   holding a distal end of a medical probe having a distal tip in a fixture;
   pressing an actuator against the distal tip, so as to apply to the distal tip multiple force vectors having respective magnitudes and angles with respect to the distal end of the probe and cause a deformation of the distal tip relative to the distal end;
   receiving from the probe first measurements indicative of the deformation of the distal tip in response to the force vectors;
   receiving from a sensing device coupled to the actuator second measurements indicative of magnitudes of the force vectors; and
   computing, based on angles and the first and second measurements, calibration coefficients for assessing the force vectors as a function of the first measurements.

10. The method according to claim 9, wherein pressing the actuator comprises pressing a planar surface coupled to the actuator against the distal tip of the probe.

11. The method according to claim 9, wherein the distal end of the probe includes a field generator that generates a magnetic field, and wherein receiving the first measurements comprises accepting the first measurements from a field sensor in the distal tip, which senses the magnetic field and produces the first measurements in response to the sensed magnetic field.

12. The method according to claim 9, wherein receiving the first measurements comprises accepting the first measurements from first and second field sensors, which are fitted respectively in the distal end and the distal tip of the probe, sense magnetic fields generated by multiple field generators external to the probe and produce the first measurements.

13. The method according to claim 9, wherein pressing the actuator comprises operating a jig holding the actuator so as to apply the force vectors at the respective magnitudes and angles.

14. The method according to claim 9, and comprising rotating the probe in the fixture with respect to a longitudinal axis of the probe, and detecting an axial asymmetry in the deformation of the distal tip by processing the first measurements received from the rotated probe.

15. The method according to claim 9, and comprising storing the calibration coefficients to a memory coupled to the probe.

16. The method according to claim 15, wherein the memory comprises an Electronically Erasable Programmable Read Only Memory.

* * * * *